United States Patent
Kirilin et al.

(10) Patent No.: US 11,548,835 B2
(45) Date of Patent: Jan. 10, 2023

(54) HYBRID CATALYST FOR SELECTIVE AND STABLE OLEFIN PRODUCTION

(71) Applicant: Dow Global Technologies LLC, Midland, MI (US)

(72) Inventors: Alexey Kirilin, Terneuzen (NL); Adam Chojecki, Terneuzen (NL); Kyle C. Andrews, Midland, MI (US); Vera P. Santos Castro, Terneuzen (NL); Aysegul Ciftci Sandikci, Eindhoven (NL); Davy L. S. Nieskens, Terneuzen (NL); Peter E. Groenendijk, Terneuzen (NL); Andrzej Malek, Midland, MI (US)

(73) Assignee: Dow Global Technologies, Midland, MI (US)

( * ) Notice: Subject to any disclaimer, the term of this patent is extended or adjusted under 35 U.S.C. 154(b) by 192 days.

(21) Appl. No.: 16/757,694

(22) PCT Filed: Oct. 11, 2018

(86) PCT No.: PCT/US2018/055422
§ 371 (c)(1),
(2) Date: Apr. 20, 2020

(87) PCT Pub. No.: WO2019/089206
PCT Pub. Date: May 9, 2019

(65) Prior Publication Data
US 2021/0371355 A1    Dec. 2, 2021

Related U.S. Application Data

(60) Provisional application No. 62/578,749, filed on Oct. 30, 2017.

(51) Int. Cl.
| | | |
|---|---|---|
| *C07C 1/04* | (2006.01) | |
| *B01J 21/06* | (2006.01) | |
| *B01J 23/06* | (2006.01) | |
| *B01J 29/85* | (2006.01) | |
| *B01J 35/10* | (2006.01) | |

(52) U.S. Cl.
CPC ............. *C07C 1/043* (2013.01); *B01J 21/063* (2013.01); *B01J 21/066* (2013.01); *B01J 23/06* (2013.01); *B01J 29/85* (2013.01); *B01J 35/1014* (2013.01); *B01J 35/1019* (2013.01); *C07C 2521/06* (2013.01); *C07C 2523/06* (2013.01); *C07C 2529/85* (2013.01)

(58) Field of Classification Search
CPC . C07C 1/043; C07C 2521/06; C07C 2523/06; C07C 2529/85; C07C 2523/04; C07C 2523/10; C07C 2523/26; C07C 2523/34; C07C 2523/72; C07C 2523/86; C07C 1/0435; B01J 21/063; B01J 21/066; B01J 23/06; B01J 29/85; B01J 35/1014; B01J 35/1019; B01J 2523/00; B01J 23/002; B01J 23/14; B01J 23/26; B01J 23/34; B01J 23/80; B01J 23/868; B01J 29/505; B01J 29/56; B01J 29/58; B01J 29/7049; B01J 29/7053; B01J 29/7065; B01J 29/72; B01J 29/7207; B01J 29/723; B01J 29/78; B01J 29/7807; B01J 29/783; B01J 29/80; B01J 35/002; Y02P 20/141; Y02P 20/52
See application file for complete search history.

(56) References Cited

U.S. PATENT DOCUMENTS

| | | |
|---|---|---|
| 4,394,297 A | 7/1983 | Kolts |
| 6,376,562 B1 | 4/2002 | Ihm et al. |
| 10,329,209 B2 | 6/2019 | Nieskens et al. |
| 10,532,961 B2 | 1/2020 | Pan et al. |
| 2018/0169623 A1* | 6/2018 | Weiss .................. B01J 29/85 |

FOREIGN PATENT DOCUMENTS

| | | |
|---|---|---|
| WO | 94006556 A1 | 3/1994 |
| WO | 2016007607 A1 | 1/2016 |
| WO | 2018045652 A1 | 3/2018 |

OTHER PUBLICATIONS

Park et al. (Hydrocarbon synthesis through CO2 hydrogenation over CuZnOZrO2/zeolite hybrid catalysts, Catalysis Today, 1998) (Year: 1998).*
Bagheri et al. (Titanium Dioxide as a Catalyst Support in Heterogeneous Catalysis, Hindawi Publishing Corporation, 2014) (Year: 2014).*
Zhu et al., "Role of Manganese Oxide in Syngas Conversion to Light Olefins", ACS Catal., 2017, 7 (4), pp. 2800-2804.

(Continued)

*Primary Examiner* — Sally A Merkling
*Assistant Examiner* — Logan Edward Laclair
(74) *Attorney, Agent, or Firm* — Dinsmore & Shohl LLP

(57) ABSTRACT

A process for preparing $C_2$ to $C_5$ olefins includes introducing a feed stream comprising hydrogen and at least one carbon-containing component selected from the group consisting of CO, $CO_2$, and mixtures thereof into a reaction zone. The feed stream is contacted with a hybrid catalyst in the reaction zone, and a product stream is formed that exits the reaction zone and includes $C_2$ to $C_5$ olefins. The hybrid catalyst includes a methanol synthesis component and a solid microporous acid component that is selected from molecular sieves having 8-MR access and having a framework type selected from the group consisting of CHA, AEI, AFX, ERI, LTA, UFI, RTH, and combinations thereof. The methanol synthesis component comprises a metal oxide support and a metal catalyst. The metal oxide support includes titania, zirconia, hafnia or mixtures thereof, and the metal catalyst includes zinc.

11 Claims, No Drawings

(56) References Cited

OTHER PUBLICATIONS

Inoue et al., "Support Effect of Zinc Oxide Catalyst on Synthesis of Methanol from CO2 and H2", Bull. Chem. Soc. Jpn., 1987, vol. 60, 2663.
Villa et al., "Synthesis of alcohols from carbon oxides and hydrogen on ZnCrTi oxides: preparation and catalytic activity", Catalysis Letters, 1992, vol. 16, 413.
Villa et al., "Synthesis of Alcohols from Carbon Oxides and Hydrogen", Applied Catalysis, 1987, vol. 35, 47.
Nomura et al., "Titania Supported Copper Catalysts for Methanol Synthesis from Carbon Dioxide", Reaction Kinetics and Catalysis Letters, 1998, vol. 63, 9.
Jiao et al., "Selective Conversion of Syngas to Light Olefins", Bao, Science, 2016, vol. 351, 1065.
International Search Report and Written Opinion pertaining to PCT/US2018/055422, dated Jan. 17, 2019.
Park et al., Hydrocarbon Synthesis through CO2 Hydrogenation Over CuZnOZrO2/zeolite Hybrid Catalysts, Catalysis Today, 1998, 44, 165-173.
Cheng et al., "Direct and Highly Selective Conversion of Synthesis Gas into Lower Olefins: Design of a Bifunctional Catalyst Combining Methanol Synthesis and Carbon-Carbon Coupling", Angew. Chem. Int. Ed., 2016, 55, 4725-4728.
Ateka et al., Direct Synthesis of Dimethyl Ether from Syngas on CuO—ZnO—MnO/SAPO-18 Bifunctional Catalyst, Int'l Journal of Hydrogen Energy, 2016, 41, 18015-18026.
Pinkaew et al., "A New Core-shell-like Capsule Catalyst with SAPO-46 Zeolite Shell Encapsulated Cr/ZnO for the Controlled Tandem Synthesis of Dimethyl Ether from Syngas", Fuel, 2013, 111, 727-732.
Examination Report pertaining to corresponding G.C.C. Patent Application No. GC 2018-36227, dated Jun. 2, 2020.

* cited by examiner

HYBRID CATALYST FOR SELECTIVE AND STABLE OLEFIN PRODUCTION

CROSS-REFERENCE TO RELATED APPLICATIONS

This application is a National Stage Entry under 35 U.S.C. 071 of International Patent Application No. PCT/US2018/055422, filed Oct. 11, 2018, which claims priority to U.S. Provisional Patent Application Ser. No. 62/578,749, filed Oct. 30, 2017, both of which are herein incorporated by reference in their entireties.

BACKGROUND

Field

The present specification generally relates to hybrid catalysts that provide selective and stable production of olefins from feed streams comprising carbon monoxide (CO), carbon dioxide ($CO_2$), and combinations thereof. More specifically, the present specification relates to a hybrid catalyst comprising a methanol synthesis component and SAPO-34 molecular sieve that provides selective and stable production of $C_2$ to $C_5$ olefins.

Technical Background

For a number of industrial applications, a desirable starting material is a lower hydrocarbon, including, in particular, $C_2$ to $C_5$ olefins that can be used to produce plastics and various downstream chemicals. These $C_2$ to $C_5$ olefin materials may include ethylene and/or propylene. A variety of processes of producing these lower hydrocarbons has been developed, including petroleum cracking and various synthetic processes.

Synthetic processes for converting feed carbon to desired products, such as hydrocarbons, are known. Some of these synthetic processes begin with the use of a hybrid catalyst. Different types of catalysts have been explored, as well as different kinds of feed streams and proportions of feed stream components. However, many of these synthetic processes have low carbon conversion, so much of the feed carbon does not get converted and exits the process in the same form as the feed carbon, or the feed carbon is converted to $CO_2$.

Accordingly, a need exists for catalysts that have a high conversion of feed carbon to desired products, such as, for example, $C_2$ to $C_5$ olefins.

SUMMARY

According to one embodiment, a process for preparing $C_2$ to $C_5$ olefins, comprises: introducing a feed stream comprising hydrogen and at least one carbon-containing component selected from the group consisting of CO, $CO_2$, and mixtures thereof into a reaction zone; contacting the feed stream with a hybrid catalyst in the reaction zone, wherein the hybrid catalyst comprises a methanol synthesis component and a solid microporous acid component that is selected from molecular sieves having 8-MR access and having a framework type selected from the group consisting of the following framework types CHA, AEI, AFX, ERI, LTA, UFI, RTH, and combinations thereof, the framework types corresponding to the naming convention of the International Zeolite Association, wherein the methanol synthesis component comprises a metal oxide support and a metal catalyst, wherein the metal oxide support comprises titania, zirconia, or mixtures thereof, and the metal catalyst comprises zinc; and forming a product stream that exits the reaction zone, wherein the product stream comprises $C_2$ to $C_5$ olefins. It should be understood that as used herein, when referring to a zinc catalyst, the zinc may be present in the form of an oxide or may be present in the form of a partially reduced oxide.

In another embodiment, a system for preparing $C_2$ to $C_5$ olefins comprises: a reaction zone comprising a hybrid catalyst, the hybrid catalyst comprising a methanol synthesis component and solid microporous acid component that is selected from molecular sieves having 8-MR access and having a framework type selected from the group consisting of the following framework types CHA, AEI, AFX, ERI, LTA, UFI, RTH, and combinations thereof, the framework types corresponding to the naming convention of the International Zeolite Association, wherein the methanol synthesis component comprises a metal oxide support and a metal catalyst, wherein the metal oxide support comprises titania, zirconia, hafnia or mixtures thereof, and the metal catalyst comprises zinc.

Additional features and advantages will be set forth in the detailed description which follows, and in part will be readily apparent to those skilled in the art from that description or recognized by practicing the embodiments described herein, including the detailed description which follows and the claims.

It is to be understood that both the foregoing general description and the following detailed description describe various embodiments and are intended to provide an overview or framework for understanding the nature and character of the claimed subject matter.

DETAILED DESCRIPTION

Methanol catalysts, such as, for example, Cr—Zn bulk mixed metal oxides, in combination with SAPO-34 molecular sieve is a hybrid catalyst that is able to convert a hydrocarbon-containing feed stream, such as, for example, syngas, to olefins. For Cr—Zn components with high activity (Zn atomic fraction>0.333, where Zn atomic fraction is defined as Zn/(Zn+Cr)) selectivity to olefins declines with time, thus decreasing overall olefin productivity. In some cases Cr—Zn (Zn atomic fraction is 0.333)—SAPO-34 hybrid catalysts have stable olefin make with time, but the overall activity of such catalysts is low. Described in the present disclosure are hybrid catalysts that address the above, as well as other, shortcomings of previously disclosed hybrid catalysts.

In embodiments, a process for preparing $C_2$ to $C_5$ olefins, comprises: introducing a feed stream comprising hydrogen gas and a carbon-containing gas into a reaction zone; contacting the feed stream with a hybrid catalyst in the reaction zone; and forming a product stream that exits the reaction zone, wherein the product stream comprises $C_2$ to $C_5$ olefins. The hybrid catalyst comprises a methanol synthesis component and SAPO-34. The methanol synthesis component comprises a metal oxide support and a metal catalyst. The metal oxide support comprises titania, zirconia, hafnia or mixtures thereof, and the metal catalyst comprises zinc.

In one or more embodiments a process for preparing $C_2$ and $C_3$ hydrocarbons comprises introducing a feed stream into a reaction zone and contacting the feed stream with a hybrid catalyst in the reaction zone. In embodiments, the feed stream comprises hydrogen gas and a carbon containing gas. The carbon containing gas may, in embodiments, be selected from carbon monoxide (CO), carbon dioxide ($CO_2$), and combinations thereof. In the feed stream, the $H_2$ gas is present in an amount of from 10 volume percent (vol %) to 90 vol %, such as from 30 vol % to 70 vol %, based on the combined volumes of the $H_2$ gas and the carbon containing gas. The feed stream may, in embodiments, be contacted with the hybrid catalyst under reaction conditions sufficient to form a product mixture, the reaction conditions comprise a reactor temperature ranging from 300 degrees Celsius (° C.) to 440° C.; a pressure of at least 15 bar (1500 kilopascals, kPa); and a gas hourly space velocity (GHSV) of at least 500 reciprocal hours ($h^{-1}$).

The hybrid catalyst, according to embodiments, comprises a methanol synthesis component in admixture with a solid microporous acid component that is selected from molecular sieves having 8-MR access and having a framework type selected from the group consisting of the following framework types CHA, AEI, AFX, ERI, LTA, UFI, RTH, and combinations thereof, the framework types corresponding to the naming convention of the International Zeolite Association. It should be understood that in embodiments, both aluminosilicate and silicoaluminophosphate frameworks may be used. In certain embodiments, the molecular sieve may be SAPO-34 silicoaluminophosphate having a CHA framework type. In one or more embodiments, the methanol synthesis component comprises a metal oxide support impregnated with a catalyst comprising a metal, a metal oxide, or mixtures thereof (hereinafter referred to as the "metal catalyst"). It is noted that certain inconsistencies in reference to mixed metal oxide-type catalysts are encountered in the art and are attributable to potential variations as to exact oxidation state(s) at the point of catalytic application, but it should be understood that any metal, such as, for example, zinc (Zn), copper (Cu), chromium (Cr), or manganese (Mn), does, in a mixed metal oxide catalyst, exist in a non-elemental oxidation state, wherein such may or may not actually form an oxide, even if it is denominated herein for convenience as simply the metal itself. It should also be understood that the designation of a specific oxide, (e.g., ZnO, does not necessarily preclude the presence of an additional or different oxide of the given metal).

As described in the present specification, embodiments include a methanol synthesis component that comprises a metal oxide support impregnated with a metal catalyst. The metal oxide support is, in embodiments, a high-surface area metal oxide support, such as, for example, a metal oxide support having a surface area from greater than or equal to 20 $m^2/g$, such as, greater than or equal to 30 $m^2/g$, greater than or equal to 40 $m^2/g$, greater than or equal to 50 $m^2/g$, or greater than or equal to 80 $m^2/g$. In one or more embodiments, a high-surface area metal oxide support, such as, for example, a metal oxide support having a surface area from greater than or equal to 20 $m^2/g$ to less than or equal to 300 $m^2/g$, such as greater than or equal to 30 $m^2/g$ to less than or equal to 300 $m^2/g$, from greater than or equal to 40 $m^2/g$ to less than or equal to 300 $m^2/g$, from greater than or equal to 50 $m^2/g$ to less than or equal to 300 $m^2/g$, or from greater than or equal to 80 $m^2/g$ to less than or equal to 300 $m^2/g$. Metal oxide supports with a high surface area, as previously described, allows for sufficient loading of the metal catalyst onto the metal oxide support.

In addition to having a high surface area, the metal oxide support used in one or more embodiments has a composition selected to improve the performance of the metal catalyst as the methanol synthesis catalyst is used and spends time on stream (i.e., is used to form hydrocarbon products form the feed stream). In embodiments, the metal oxide support may comprise, consist essentially of, or consist of a metal oxide selected from titanium dioxide (titania or $TiO_2$), zirconium dioxide (zirconia or $ZrO_2$), or Hafnia ($HfO_2$) and mixtures thereof. In some embodiments the metal oxide support comprises titania. The titania may, in some embodiments, be a polymorph that contains mostly anatase phase, rutile phase, brookite phase, or mixtures thereof. In some embodiments, the metal oxide support comprises zirconia. The zirconia may, in embodiments, have a tetragonal phase crystalline structure or a monoclinic phase crystalline structure, cubic crystalline structure, or mixtures thereof. In one or more embodiments, the zirconia may be doped with components such as lanthanum (La), sulfate ($SO_4$), yttria oxide ($Y_2O_3$), ceria oxide ($CeO_2$), silica ($SiO_2$), tungsten (W) and mixtures thereof to stabilize a monoclinic or a tetragonal phase.

In one or more embodiments, the metal oxide support may comprise a mixture of titania and zirconia. In such embodiments, the metal oxide support may comprise from greater than to 0 weight percent (wt %) to less than or equal to 100 wt % zirconia, such as from greater than or equal to 50 wt % to less than or equal to 70 wt % zirconia, or about 60 wt % zirconia. Accordingly, in such embodiments, the metal oxide support may comprise from greater than or equal to 20 wt % to less than or equal to 60 wt % titania, such as from greater than or equal to 30 wt % to less than or equal to 50 wt % titania, or about 40 wt % titania.

It should be understood that titania may include trace amounts of impurities in some embodiments while still being referred to herein as a titania support. For instance, a titania support, as described herein, may include less than 3 wt % sulfur, less than 5 wt % alumina, less than 5 wt % silica, less than 1 wt % iron oxide, less than 1 wt % hydrochloric acid, and less than 5 wt % calcium.

As described previously, the methanol synthesis component comprises a metal catalyst impregnated onto the metal oxide support. In embodiments the metal catalyst comprises, consists essentially of, or consists of zinc. It should be understood that as used herein, when referring to a zinc catalyst, the zinc may be present in the form of an oxide or may be present in the form of a partially reduced oxide. In addition to zinc, other metals may be included in the metal catalyst. For instance, in one or more embodiments, the metal catalyst may comprise a metal selected from copper (Cu), chromium (Cr), manganese (Mn), tin (Sn), vanadium (V), iron (Fe), scandium (Sc), yttrium (Y), lanthanum (La), niobium (Nb), tantalum (Ta), manganese (Mn), rhenium (Re), silver (Ag), gold (Au), cadmium (Cd), gallium (Ga), indium (In), lead (Pb), nickel (Ni), bismuth (Bi), and mixtures thereof in addition to zinc. It should be understood that, as previously disclosed, these metals may be present in the metal catalyst as a metal, as a metal oxide, or as a mixture of metal and metal oxide. In some embodiments, the atomic fraction of zinc in the metal catalyst (where the sum of all metal catalyst components is equal to one (1.00)) is from greater than or equal to 0.25 to less than or equal 1.00, such as from greater than or equal to 0.33 to less than or equal to 0.75, from greater than or equal to 0.40 to less than or equal to 0.60, or about 0.50. Accordingly, in such embodiments, the atomic fraction of the sum of the remaining metal catalysts (i.e., metal catalysts other than zinc) is from greater than or equal to 0.00 to less than or equal to 0.75, such as from greater than or equal to 0.25 to less than or equal to 0.66, from greater than or equal to 0.40 to less than or equal to 0.60, or about 0.50. In some embodiments, the metal catalyst is zinc (i.e., having an atomic fraction of zinc to remaining metal catalysts of 1.00). It should be understood that metals in the metal oxide support are not considered in the atomic fraction of zinc in the metal catalyst.

The metal catalyst may be deposited onto metal oxide support by any suitable method. For example, common techniques include but not limited to: incipient wetness impregnation, impregnation with excess of solution followed by removal of solvent (water) under vacuum and/or heating (using rotavapor instrument for example), surfactant-assisted impregnation, chemical vapor deposition (liquid or gas phase), precipitation in the presence of support. In embodiments, an aqueous solution comprising the metal catalyst components may be formulated, and the aqueous solution is contacted to the metal oxide support material. The metal catalyst component (precursor) may be added to the solution in any suitable form. For example, in some embodiments a nitrate of the metal catalyst component is introduced into the aqueous solution (i.e., zinc (II) nitrate, chromium (III) nitrate, and/or manganese (II) nitrate are added to an aqueous solution) and contacted with the metal oxide support. Other commonly available metal catalyst salts (precursors) that can be used in embodiments include: acetate, chloride (and other halides), carbonate (if soluble), formate, triflate, etc. The aqueous solution comprising the metal catalyst is contacted to the metal oxide support under such conditions (e.g., concentration of metal catalyst in the aqueous solution, temperature, pressure, agitation) and for such a time that the desired loading of the metal catalyst in the metal oxide support is achieved. For instance, in some embodiments, one impregnation step is required to reach the desired loading, while in other embodiment two impregnations steps are required to reach the desired loading. It should be understood that the process for impregnating the metal oxide support with the metal catalyst is not limited and can be selected to achieve the desired loading.

In one or more embodiments, the loading of the metal catalyst, which is measured per 100 mg of metal oxide support, is from greater than or equal to 0.8 mg of metal catalyst/100 mg of metal oxide support to less than or equal to 50.0 mg of metal catalyst/100 mg of metal oxide support, such as from greater than or equal to 4.0 mg of metal catalyst/100 mg of metal oxide support to less than or equal to 40.0 mg of metal catalyst/100 mg of metal oxide support, from greater than or equal to 10.0 mg of metal catalyst/100 mg of metal oxide support to less than or equal to 30.0 mg of metal catalyst/100 mg of metal oxide support, or from greater than or equal to 15.0 mg of metal catalyst/100 mg of metal oxide support to less than or equal to 20 mg of metal catalyst/100 mg of metal oxide support.

After the metal oxide support is impregnated with the metal catalyst precursor, the impregnated metal oxide support may be thermally treated at elevated temperature. The treatment can be carried out in varied atmospheres: air, inert (nitrogen) or reducing atmosphere (hydrogen, syngas). In one or more embodiments, the impregnated metal oxide support is calcined in air at a temperature that is less than 800° C., such as at a temperature within a range from greater than or equal to 300° C. to less than 750° C., from greater than or equal to 350° C. to less than or equal to 600° C., from greater than or equal to 375° C. to less than or equal to 500° C., or about 400° C.

In embodiments, one or more promoters may be added into the metal oxide support in addition to the metal catalyst components. The promoters added into the metal oxide support are not metal-containing, and do not contribute to the atomic fraction of the metal catalyst previously disclosed herein. The one or more promoters may include, in embodiments, an element selected from the group consisting of sulfates, sulfur, alkaline earth metals (such as, for example, calcium and magnesium and other alkaline earth elements), phosphates, boron, halides (such as, for example, chlorine and fluorine), alkali metals (such as, for example, potassium and sodium), and mixtures thereof. In some embodiments, the promoters may include a member of the group consisting of silicon (Si), germanium (Ge), arsenic (As), antimony (Sb), selenium (Se), carbon (C), and mixtures thereof. The one or more promoters are added as a molar proportion of zinc present in the metal catalyst. In some embodiments, the one or more promoter is added in an amount from greater than or equal to 1 mol promoter/100 mol zinc to less than 50 mol promoter/100 mol zinc, such as from greater than or equal to 10 mol promoter/100 mol zinc to less than or equal to 15 mol promoter/100 mol zinc. The one or more promoters are added into the metal oxide support by contacting a solution comprising the one or more promoters to a metal oxide support. This can be done by any suitable method and with any suitable solution. It should also be understood that the metal oxide support may be impregnated with the one or more promoters simultaneously with the metal catalyst, or the metal oxide support may be impregnated with the one or more promoters before or after the metal oxide support is impregnated with the metal catalyst.

The methanol synthesis component and the molecular sieve are, in one or more embodiments, present in a reaction zone, in a weight/weight (wt/wt) ratio (methanol synthesis component:molecular sieve) ranging from greater than or equal to 0.1:1 to less than or equal to 10:1, such as from greater than or equal to 0.5:1 to less than or equal to 9:1.

In one or more embodiments, the hybrid catalyst comprises, consists essentially of, or consists of a titania metal oxide support, a zinc metal catalyst, and SAPO-34 molecular sieve. In such embodiments, the atomic ratio (at/at) of zinc to titania (Zn/Ti) is from greater than or equal to 0.01 to less than or equal to 0.61, such as from greater than or equal to 0.02 to less than or equal to 0.40, from greater than or equal to 0.03 to less than or equal to 0.35, from greater than or equal to 0.04 to less than or equal to 0.30, from greater than or equal to 0.05 to less than or equal to 0.25, or from greater than or equal to 0.06 to less than or equal to 0.20. In other embodiments the atomic ratio of zinc to titania is from greater than or equal to 0.01 to less than or equal to 0.10, such as from greater than or equal to 0.02 to less than or equal to 0.09, from greater than or equal to 0.03 to less than or equal to 0.08, or from greater than or equal to 0.04 to less than or equal to 0.07.

In some embodiments, the hybrid catalyst comprises, consists essentially of, or consists of a zirconia metal oxide support, a zinc metal catalyst, and SAPO-34 molecular sieve. In such embodiments, the atomic ratio of zinc to zirconia (Zn/Zr) is from greater than or equal to 0.01 to less than or equal to 0.94, such as from greater than or equal to 0.04 to less than or equal to 0.08, or about 0.06.

Using a hybrid catalyst as previously described provides a number of advantages over hybrid catalysts disclosed in literature. In particular the hybrid compositions described herein provide a combination of improved carbon monoxide conversion, improved carbon yield of $C_2$ to $C_5$ olefins, and improved integral productivity; each of which will be described in more detail below.

Carbon monoxide conversion ($X_{CO}$) is defined herein as a percent of carbon in all hydrocarbons produced in the reaction zone to the total amount of carbon released from the reaction zone. The carbon monoxide conversion is measured as an average of all data points for a time-on-stream in the rage of 20 to 40 hours. The formula for calculating the carbon monoxide conversion is as follows in Equation 1:

$$X_{CO} = \frac{C_{prod}}{C_{total}} \times 100 \tag{1}$$

In Equation 1, $X_{CO}$ is the carbon monoxide conversion, $C_{prod}$ is the amount of carbon (in mol %) in hydrocarbons produced in the reaction zone, and $C_{total}$ is the total amount of carbon exiting the reaction zone. In embodiments, the carbon monoxide conversion, in mol %, is greater than or equal to 15%, such as greater than or equal to 18%, greater than or equal to 20%, greater than or equal to 22%, greater than or equal to 24%, greater than or equal to 26%, greater than or equal to 28%, greater than or equal to 30%, greater than or equal to 32%, greater than or equal to 34%, greater than or equal to 36%, greater than or equal to 38%, or greater than or equal to 40%. The carbon monoxide conversion for each of the above ranges may, in some embodiments, be less than or equal to 100%.

The carbon selectivity of product i is calculated as follows:

$$S_i = \frac{c_i}{c_{prod}} \times 100 \tag{2}$$

where $C_{prod}$ is the amount of carbon (in mol %) in carbon-containing products produced in the reaction zone, and $C_i$ is the total amount of carbon exiting in the product i. For simplicity $CO_2$ is also considered as product when syngas contains only carbon monoxide and hydrogen.

The olefin yield, paraffin yield, or methane yield ($Y_1$) may be calculated as follows:

$$Y_i = X_{CO}/100 \times S_i \tag{3}$$

Conversion, selectivities and yields were calculated as a mean value using 20-40 hour time-on-stream range. Equation 3 shows how to calculate the carbon yield of olefins, paraffins, or methane. In embodiments, the yield of C2 to C5 olefins (in mol %) is greater than or equal to 3.6%, greater than or equal to 6.0%, greater than or equal to 8.0%, greater than or equal to 10.0%, greater than or equal to 12.0%, or greater than or equal to 14.0%. The yield of C2 to C5 olefins for each of the above ranges may, in some embodiments, be less than or equal to 100.0%.

The productivity of the hybrid catalyst is the amount of $C_2$ to $C_5$ olefins produced compared to the amount of catalyst used to form the $C_2$ to $C_5$ olefins. The productivity may be measured using the following Equation 4:

$$P_{olefins} = \frac{F \times 60 \times f}{V_m \times V_{cat}/1000} \times \frac{X_{CO}}{100} \times \sum_{i=2}^{5} \frac{S_{Mi} \times Mi}{100} \tag{4}$$

In Equation 4, $P_{olefins}$ is the productivity, f is the volume fraction of CO in syngas, F is the total flow of synthesis gas through a catalyst bed ($cm^3$/min at STP (standard temperature and pressure)), $V_m$ is the molar volume of gas under normal conditions (22400 $cm^3$/mol), $V_{cat}$ is catalyst volume including interparticle void space or reactor bed volume ($cm^3$), $X_{CO}$ is the carbon monoxide conversion, $S_{Mi}$ is molar selectivity (calculated per Equation 5), and Mi is a molecular weight of component i [g/mol].

$S_{Mi}$ may be calculated as follows:

$$S_{Mi} = \frac{v_i}{\sum_{i=1}^{k} v_i} \times 100 \tag{5}$$

where vi is the number of moles of product i produced in the reaction zone and $\sum_{i=1}^{k} v_i$ –sum of moles of carbon-containing products i-k produced in the reaction zone ($CO_2$, methane, $C_2$-$C_5$ paraffins, $C_2$-$C_5$ olefins).

The productivity calculated by Equation 4 is the productivity at any given time during the process of forming $C_2$ to $C_5$ olefins in the reaction zone. However, the productivity calculated using Equation 4 does not indicate the productivity of the hybrid catalyst during the entire time-on-stream. To evaluate the productivity of the hybrid catalyst during the entire time-on-stream, integral productivity is determined.

The integral productivity is determined using a linear extrapolation of a plurality of productivity ($P_{olefins}$) values. A plurality of $P_{olefins}$ values are measured at various times and plotted on graph where the y=axis is $P_{olefins}$ and the x-axis is time. Once a sufficient plurality of $P_{olefins}$ values are plotted, an accurate linear extrapolation of the values of $P_{olefins}$ may be determined where the linear extrapolation extends from time equal to zero (0) to a time where a predetermined minimum $P_{olefins}$ value is reached. Coefficient of linear extrapolation $P_{slope}$ was calculated using data from a time-on-stream-range of 20-100 h. Once the linear extrapolation is complete, the slope of the line may be determined by fitting the linear extrapolation to a linear function provided in Equation 6 as follows:

$$P_{olefins} = P_{slope} \times t + P_0 \tag{6}$$

In Equation 6, $P_{olefins}$ is the productivity of the olefins at a specific time, $P_{slope}$ is the slope of the linear extrapolation previously described, t is time, and $P_0$ is the productivity at time equal to 0. Using the above linear function, $P_{slope}$ may be calculated. It should be understood that a skilled artisan is capable of determining when a sufficient number of $P_{Olefin}$ values have been calculated to obtain an accurate linear extrapolation, a skilled artisan would be able to perform the linear extrapolation, and a skilled artisan would be able to determine the slope of the linear function.

Once $P_{slope}$ is determined, the integral productivity of the hybrid catalyst may be determined. First, it is determined whether $P_{slope}$ is greater than or equal to 0 ($P_{slope} \geq 0$). If $P_{slope} \geq 0$, then the integral productivity is calculated using Equation 7 as follows:

$$P_{int} = P_0 \times 1000 \tag{7}$$

In Equation 7, $P_{int}$ is the integral productivity and $P_0$ is the productivity at time equals 0.

However, if $P_{slope}$ is less than 0 ($P_{slope} < 0$), then the integral productivity is determined by calculating the time when the productivity equals 0 ($t_{p=0}$). The value $t_{p=0}$ can be calculated using Equation 8 as follows:

$$t_{p=0} = \frac{-P_0}{P_{slope}} \tag{8}$$

Once the value for $t_{p=0}$ is determined, it can be used to calculate the integral productivity for cases where $P_{slope}$ was previously calculated to be less than 0. If $t_{p=0}$ is less than 1000 hours ($t_{p=0} < 1000$ hrs), the integral productivity ($P_{int}$) may be calculated using Equation 9 as follows:

$$P_{int} = P_0 \times \frac{t_{p=0}}{2} \quad (9)$$

However, if $t_{p=0}$ is greater than or equal to 1000 hours ($t_{p=0} \geq 1000$ hrs), then $P_{int}$ may be calculated using Equation 10 as follows:

$$P_{int} = \frac{P_0^2}{2 \times P_{slope}} \times (-1) - \frac{(P_0 + P_{slope} \times 1000)^2}{2 \times P_{slope}} \times (-1) \quad (10)$$

In embodiments, the integral productivity of the hybrid catalyst (calculated for a time-on-stream range of 1000 h) is greater than or equal to 2.5 kg olefins/liter (1) of catalyst, such as greater than or equal to 2.7 kg olefins/1 of catalyst, greater than or equal to 3.0 kg olefins/1 of catalyst, greater than or equal to 3.5 kg olefins/1 of catalyst, greater than or equal to 4.0 kg olefins/1 of catalyst, greater than or equal to 4.5 kg olefins/1 of catalyst, greater than or equal to 5.0 kg olefins/1 of catalyst, greater than or equal to 5.5 kg olefins/1 of catalyst, greater than or equal to 6.0 kg olefins/1 of catalyst, greater than or equal to 6.5 kg olefins/1 of catalyst, greater than or equal to 7.0 kg olefins/1 of catalyst, greater than or equal to 7.5 kg olefins/1 of catalyst, greater than or equal to 8.0 kg olefins/1 of catalyst, greater than or equal to 10.0 kg olefins/1 of catalyst, greater than or equal to 12.0 kg olefins/1 of catalyst, greater than or equal to 14.0 kg olefins/1 of catalyst, greater than or equal to 16.0 kg olefins/1 of catalyst, greater than or equal to 18.0 kg olefins/1 of catalyst, greater than or equal to 20.0 kg olefins/1 of catalyst, greater than or equal to 22.0 kg olefins/1 of catalyst, greater than or equal to 24.0 kg olefins/1 of catalyst, or greater than or equal to 26.0 kg olefins/1 of catalyst. It should be understood that the integral productivity of the hybrid catalyst is only limited by the process conditions and parameters.

However, in some embodiments, the integral productivity for any of the above ranges may be less than or equal to 80.0 kg olefins/1 of catalyst, such as less than or equal to 40.0 kg olefins/1 of catalyst.

EXAMPLES

Embodiments will be further clarified by the following examples.

The preparation of methanol synthesis components of the hybrid catalyst will first be described for each of the examples and comparative examples.

Example 1

Stock solution of zinc nitrate in water with concentration of 2 mol/1 was prepared. Titania support (NORPRO, Anatase, ST61120, BET surface area 130 m²/g) was crushed and sieved to 60-80 mesh size. Pore volume of the support for incipient wetness impregnation was determined, with water, to be 0.57 ml/g. Total loading of zinc on the support was 4 mg (as zinc oxide) per 100 mg of support.

A solution for impregnation containing zinc was prepared by mixing an aliquot of the stock Zn nitrate solution with deionized water in the proportion required to achieve target loading of zinc on the support. Subsequently, 2 g of the support were impregnated with 1.14 ml of the solution with continuous shaking. One impregnation step was required. The as-prepared material was dried and calcined using the following steps: (1) heated from room temperature (RT) to 120° C. at 2° C./min; (2) dwell for 2 hrs at 120° C.; (3) heated from 120° C. to 400° C. at 2° C./min; (4) dwell for 4 hrs; and (5) cooled down to RT in 2 hrs After calcination, the catalyst was re-sieved to 60-80 mesh size to remove fine particles.

Example 2

Prepared in the same way as the Example 1, except the total loading was 10 mg (zinc oxide) per 100 mg of support.

Example 3

Prepared in the same way as the Example 1, except the total loading was 40 mg zinc oxide per 100 mg of support, and to achieve the target loading 2 impregnations were required. The catalyst was dried between impregnations for 2 hrs at 120° C. in air. After the second impregnation the catalyst was dried, calcined, and relieved as in Example 1.

Example 4

Prepared in the same way as Example 1, except a different titania support (NORPRO, Anatase, ST31119, BET surface area 40 m²/g, pore volume 0.43 ml/g) was used. The total loading was 4 mg (zinc oxide) per 100 mg of support.

Example 5

Prepared in the same way as Example 1, except a different titania support (rutile phase (purity confirmed by XRD), BET surface area around 100 m²/g, pore volume 0.50 ml/g) was used. The total loading was 5 mg zinc oxide per 100 mg of support.

Example 6

Two separate stock solutions were prepared: chromium (III) nitrate in water at a concentration of 2 mol/1, and zinc (II) nitrate in water at a concentration of 2 mol/1. A titania support (NORPRO, Anatase, ST61120, BET surface area 130 m²/g) was sieved to 60-80 mesh size. The pore volume of the support for impregnation was determined, with water, to be 0.57 ml/g. The total loading of oxides was 4 mg of ($Cr_2O_3$+ZnO) per 100 mg of support. An atomic ratio of Cr/Zn ratio was 4/10.

The solution for impregnation containing zinc and chromium was prepared by mixing aliquots of the stock Zn nitrate and the stock Cr nitrate solutions with deionized water in the proportion required to achieve target loading of zinc and chromium on the support. Subsequently, 2 g of the support were impregnated with 1.14 ml of the solution with continuous shaking. One impregnation step was required. The as-prepared material was dried and calcined using the following steps: (1) heated from RT to 120° C. at 2° C./min; (2) dwell for 2 hrs at 120° C.; (3) heated from 120° C. to 500° C. at 2° C./min; (4) dwell for 4 hrs; and (5) cooled down to RT in 2 hrs. After calcination the catalyst was re-sieved to 60-80 mesh size to remove fine particles.

Example 7

Prepared in the same way as Example 6, except Cr was replaced with Mn. Target Mn/Zn atomic ratio was 2/1, and the calcination temperature was 500° C.

Example 8

Two stock solutions were prepared: zinc (II) nitrate in water at a concentration of 2 mol/1 and ammonium sulfate in water at a concentration of 0.3 mol/l. A titania support (NORPRO, Anatase, ST61120, BET surface area 130 m$^2$/g) was sieved to 60-80 mesh size. The pore volume for impregnation was determined experimentally, with water, to be 0.57 ml/g. The total loading of zinc was 4 mg (zinc oxide) per 100 mg of support. An atomic ratio of $SO_4$/Zn was 15/100.

The solution for impregnation was prepared by mixing aliquots of the stock Zn nitrate and the stock ammonium sulfate solutions with water in the proportion required to achieve target loading of zinc and the sulfate on the support. Subsequently, 2 g of the support were impregnated with 1.14 ml of the solution with continuous shaking. One impregnation step was required. The as-prepared material was dried and calcined using the following steps: (1) heated from RT to 120° C. at 2° C./min; (2) dwell for 2 hrs; (3) heated from 120° C. to 400° C. at 2° C./min; (4) dwell for 4 hrs; and (5) cooled down to RT in 2 hrs. After calcination the catalyst was re-sieved to 60-80 mesh size to remove fine particles.

Example 9

Two stock solutions were prepared: zinc (II) nitrate in water at a concentration of 2 mol/l and ammonium sulfide in water at a concentration of 0.3 mol/l. A titania support (NORPRO, Anatase, ST61120, BET surface area 130 m$^2$/g) was sieved to 60-80 mesh size. The pore volume for impregnation was determined experimentally with water to be 0.57 ml/g. The total loading of zinc was 4 mg (zinc oxide) per 100 mg of support. An atomic ratio of S/Zn was 10/100.

A solution for impregnation containing zinc was prepared by mixing an aliquot of the stock Zn nitrate solution with deionized water in the proportion required to achieve target loading of zinc on the support. Separately, a solution for impregnation containing ammonium sulfide was prepared by mixing an aliquot of the ammonium sulfide stock solution with water in the proportion required to achieve the target loading of sulfide in the catalyst.

First, 2 g of the support were impregnated with 1.14 ml of the zinc solution. The material was dried for 2 hrs at 120° C. Subsequently, the material was impregnated with 1.14 ml of the ammonium sulfide solution. The as-prepared material was dried and calcined using the following steps: (1) heated from RT to 120° C. at 2° C./min; (2) dwell for 2 hrs; (3) heated from 120° C. to 400° C. at 2° C./min; (4) dwell for 4 hrs; and (5) cooled down to RT in 2 hrs. After calcination the catalyst was re-sieved to 60-80 mesh size to remove fine particles.

Example 10

Prepared in the same way as Example 1, except that the titania support was TI 1100 E (BASF, anatase, BET surface area 110 m$^2$/g, containing 3 wt % Ca and 2.2% S, pore volume 0.5 ml/g). The total loading was 4 mg (zinc oxide) per 100 mg of support.

Example 11

Prepared in the same way as Example 8, except ammonium sulfate was replaced with ammonium hydrogen phosphate. The total loading of zinc was 4 mg (zinc oxide) per 100 mg of support. The atomic ratio of P/Zn was 15/100.

Example 12

Prepared in the same way as Example 8, except ammonium sulfate was replaced with ammonium pentaborate (concentration of 0.1 mol/l). Total loading of zinc was 4 mg (zinc oxide) per 100 mg of support. The atomic ratio of B/Zn was 15/100.

Example 13

Prepared in the same way as Example 8, except ammonium sulfate was replaced with ammonium chloride. Total loading of zinc was 4 mg zinc oxide per 100 mg of support. The atomic ratio of Cl/Zn was 5/100.

Example 14

Prepared in the same way as Example 8, except ammonium sulfate was replaced with potassium nitrate. Total loading of zinc was 4 mg zinc oxide per 100 mg of support. The atomic ratio of K/Zn was 10/100.

Example 15

A CuCrZn/TiO$_2$ catalyst was prepared by the incipient wetness impregnation method. A precursor solution containing Cu(NO$_3$)$_2$.3H$_2$O, Cr(NO$_3$)$_2$.9H$_2$O and Zn(NO$_3$)$_2$.6H$_2$O was prepared targeting Cu, Cr and Zn loadings of 2.5, 2.5, and 5 wt %, respectively. Total metal oxides loading was 15 mg per 100 mg of support. The precursor solution was impregnated on a titania support (NORPRO, Anatase, ST61120). After drying overnight at 100° C., the catalyst was calcined in static oven at 400° C. for 2 hrs.

Example 16

A CuZn/TiO$_2$ catalyst was prepared by incipient wetness impregnation method. A precursor solution containing Cu(NO$_3$)$_2$.3H$_2$O and Zn(NO$_3$)$_2$.6H$_2$O was prepared targeting Cu and Zn loadings of 5 wt % each. Total metal oxides loading was 14.3 mg per 100 mg of support. The precursor solution was impregnated on a titania support (NORPRO, Anatase, ST61120). After drying overnight at 100° C., the catalyst was calcined in static oven at 400° C. for 2 hrs.

Example 17

A CrZn/TiO$_2$ catalyst was prepared by incipient wetness impregnation method. A precursor solution containing Cr(NO$_3$)$_2$.9H$_2$O and Zn(NO$_3$)$_2$.6H$_2$O was prepared targeting Cr and Zn loadings of 5 wt % each. Total metal oxides loading was 15.7 mg per 100 mg of support. The precursor solution was impregnated on a titania support (NORPRO, Anatase, ST61120). After drying overnight at 100° C., the catalyst was calcined in static oven at 400° C. for 2 hrs.

Example 18

Prepared in the same way as Example 1, except a zirconia support (NORPRO, monoclinic, SZ39114, BET surface area 50 m$^2$/g, pore volume 0.44 ml/g) was used in place of the titania support. The total loading was 4 mg zinc oxide per 100 mg of support.

Example 19

Prepared in the same way as Example 1, except a zirconia support (NORPRO, tetragonal, SZ61152, BET surface area 140 m$^2$/g, pore volume 0.34 ml/g) was used in place of the titania support. The total loading was 4 mg zinc oxide per 100 mg of support.

Example 20

Prepared in the same way as Example 1, except a zirconia-titania mixed phase (60 wt % tetragonal $ZrO_2$— 40 wt % anatase $TiO_2$) support (NORPRO, SZ39140, BET surface area 80 $m^2/g$, pore volume 0.57 ml/g) was used in place of the titania support. The total loading was 4 mg zinc oxide per 100 mg of support.

Example 21

Prepared in the same way as Example 1, except a La-doped zirconia (containing 6.5 wt % $La_2O_3$) support (NORPRO, tetragonal, SZ61156, BET surface area 120 $m^2/g$, pore volume 0.40 ml/g) was used in place of the titania support. The total loading was 4 mg zinc oxide per 100 mg of support.

Example 22

Prepared in the same way as Example 1, except a sulfated zirconia (contains 3.3 wt % $SO_3$, 2.7 wt % % $SiO_2$) support (NORPRO, tetragonal, SZ61192, BET surface area 130 $m^2/g$, pore volume 0.39 ml/g) was used in place of the titanium support. The total loading was 4 mg zinc oxide per 100 mg of support.

Example 23

Prepared in the same way as the Example 1, except the total loading was 1 mg (zinc oxide) per 100 mg of support.

Example 24

Prepared in the same way as the Example 1, except the supports was titania with surface area of 285 $m^2/g$ (pore volume determined with DI water is 0.79 ml/g). Total loading was 5.2 mg (zinc oxide) per 100 mg of support.

Example 25

Prepared in the same way as the Example 1, except the support was mesoporous hafnium oxide (hafnia, $HfO_2$) with surface area of 32 $m^2/g$ (pore volume determined with DI water is 0.22 ml/g). Total loading was 2.6 mg (zinc oxide) per 100 mg of support.

TABLE 1

Composition of Examples 1-25

| Example | M1 | M2 | M3 | M1 atomic fraction | M2 atomic fraction | M3 atomic fraction | Total oxides loading per support, mg/100 mg of support | Promoter | Promoter level, mol/mol$_{Zn}$ |
|---|---|---|---|---|---|---|---|---|---|
| 1 | Zn | — | — | 1 | — | — | 4 | — | — |
| 2 | Zn | — | — | 1 | — | — | 10 | — | — |
| 3 | Zn | — | — | 1 | — | — | 40 | — | — |
| 4 | Zn | — | — | 1 | — | — | 4 | — | — |
| 5 | Zn | — | — | 1 | — | — | 5 | — | — |
| 6 | Zn | Cr | — | 0.7143 | 0.2857 | — | 4 | — | — |
| 7 | Zn | Mn | — | 0.3333 | 0.6667 | — | 4 | — | — |
| 8 | Zn | — | — | 1 | — | — | 4 | $SO_4$ | 15 |
| 9 | Zn | — | — | 1 | — | — | 4 | S | 10 |
| 10 | Zn | — | — | 1 | — | — | 4 | Ca, S* | — |
| 11 | Zn | — | — | 1 | — | — | 4 | $PO_4$ | 15 |
| 12 | Zn | — | — | 1 | — | — | 4 | B | 15 |
| 13 | Zn | — | — | 1 | — | — | 4 | Cl | 5 |
| 14 | Zn | — | — | 1 | — | — | 4 | K | 10 |
| 15 | Cu | Cr | Zn | 0.24 | 0.29 | 0.47 | 15 | — | — |
| 16 | Cu | Zn | — | 0.51 | 0.49 | — | 14.3 | — | — |
| 17 | Zn | Cr | — | 0.44 | 0.56 | — | 15.7 | — | — |
| 18 | Zn | — | — | 1 | — | — | 4 | — | — |
| 19 | Zn | — | — | 1 | — | — | 4 | — | — |
| 20 | Zn | — | — | 1 | — | — | 4 | — | — |
| 21 | Zn | — | — | 1 | — | — | 4 | — | — |
| 22 | Zn | — | — | 1 | — | — | 4 | — | — |
| 23 | Zn | — | — | 1 | — | — | 1 | — | — |
| 24 | Zn | — | — | 1 | — | — | 5.2 | — | — |
| 25 | Zn | — | — | 1 | — | — | 2.6 | — | — |

| Example | Support | Support Phase | Support surface area, $m^2/g$ | M1 mmol/g support | M2 mmol/g support | M3 mmol/g support | Zn/Ti at/at | Zn/Zr at/at | Calc. T, ° C. |
|---|---|---|---|---|---|---|---|---|---|
| 1 | titania | Anatase | 130 | 0.489 | — | — | 0.0391 | — | 400 |
| 2 | titania | Anatase | 130 | 1.223 | — | — | 0.0977 | — | 400 |
| 3 | titania | Anatase | 130 | 4.894 | — | — | 0.3909 | — | 400 |
| 4 | titania | Anatase | 40 | 0.489 | — | — | 0.0391 | — | 400 |
| 5 | titania | Rutile | 100 | 0.612 | — | — | 0.0488 | — | 400 |
| 6 | titania | Anatase | 40 | 0.358 | 0.143 | — | 0.0286 | — | 500 |
| 7 | titania | Anatase | 130 | 0.221 | 0.442 | — | 0.0176 | — | 400 |
| 8 | titania | Anatase | 130 | 0.489 | — | — | 0.0391 | — | 400 |
| 9 | titania | Anatase | 130 | 0.489 | — | — | 0.0391 | — | 400 |
| 10 | titania | Anatase | 110 | 0.489 | — | — | 0.0391 | — | 400 |

TABLE 1-continued

Composition of Examples 1-25

| | | | | | | | | | |
|---|---|---|---|---|---|---|---|---|---|
| 11 | titania | Anatase | 130 | 0.489 | — | — | 0.0391 | — | 400 |
| 12 | titania | Anatase | 130 | 0.489 | — | — | 0.0391 | — | 400 |
| 13 | titania | Anatase | 130 | 0.489 | — | — | 0.0391 | — | 400 |
| 14 | titania | Anatase | 130 | 0.489 | — | — | 0.0391 | — | 400 |
| 15 | titania | Anatase | 130 | 0.437 | 0.534 | 0.849 | 0.0679 | — | 400 |
| 16 | titania | Anatase | 130 | 0.875 | 0.849 | — | 0.0679 | — | 400 |
| 17 | titania | Anatase | 130 | 0.849 | 1.068 | — | 0.0679 | — | 400 |
| 18 | zirconia | monoclinic | 50 | 0.489 | — | — | — | 0.06 | 400 |
| 19 | zirconia | tetragonal | 140 | 0.489 | — | — | — | 0.06 | 400 |
| 20 | Zirconia-titania** | Tetragonal-anatase | 80 | 0.489 | — | — | 0.0976 | 0.1 | 400 |
| 21 | zirconia | La-doped tetragonal | 120 | 0.489 | — | — | — | 0.06 | 400 |
| 22 | zirconia | Sulfated tetragonal | 130 | 0.489 | — | — | — | 0.06 | 400 |
| 23 | titania | Anatase | 130 | 0.098 | — | — | 0.01 | — | 400 |
| 24 | titania | Anatase | 285 | 0.6357 | — | — | 0.05 | — | 400 |
| 25 | Hafnia | — | 32 | 0.32 | — | — | — | — | 400 |

*$TiO_2$ support contains 3 wt % of Ca and 2.2 wt % of S
**60 wt % $ZrO_2$ (tetragonal) and 40 wt % $TiO_2$ (anatase)

Comparative Example 1

Commercially available Cu-based methanol synthesis catalyst HiFuel™ manufacture by Johnson Matthey was used. The catalyst was crushed and sieved to 60-80 mesh size.

Comparative Example 2

Prepared in the same way as Example 6, except the support was silica (Davidson 57, 290 m$^2$/g, pore volume determined to be 1.2 ml/g). Total loading of oxides was 20 mg of ($Cr_2O_3$+ZnO) per 100 mg of support. The atomic Cr/Zn ratio was 4/10. The material was calcined in air at 500° C. for 4 hrs.

Comparative Example 3

Prepared in the same way as Comparative Example 2, except the atomic Cr/Zn ratio was 2/1.

Comparative Example 4

Prepared in the same way as Example 6, except the support was ceria (68 m$^2$/g, pore volume determined to be 0.3 ml/g). Total loading of oxides was 4 mg of ($Cr_2O_3$+ZnO) per 100 mg of support. The atomic Cr/Zn ratio was 4/10. The material was calcined in air at 500° C. for 4 hrs.

Comparative Example 5

Prepared in the same way as Comparative Example 4, except the atomic Cr/Zn ratio was 2/1.

Comparative Example 6

In this comparative example, the catalyst was prepared by rotavapor method. Initially 5 g of a titania support (fines<80 mesh size, NORPRO, Anatase, ST61120, BET surface area 130 m$^2$/g, pore volume 0.57 ml/g) were placed in 500 ml round bottom flask followed by 57.35 ml of 2 M zinc nitrate solution in DI water. The flask was connected to a rotavaporator and placed in the water bath (80° C.). The mixture was rotated under vacuum for 6 hrs until most of water was removed and a high viscous paste was formed. The rest of water was removed under vacuum in the vacuum oven (20 mbar, 80° C.) overnight. The as-prepared mixture was dried and calcined using the following steps: (1) heated from RT to 120° C. at 2° C./min; (2) dwell for 2 hrs; (3) heated from 120° C. to 400° C. at 2° C./min; (4) dwell for 4 hrs; and (5) cooled down to RT in 2 hrs. After calcination the catalyst powder was pelletized, crushed and sieved to 60-80 mesh size. Elemental analysis (XRF) showed that the material contains 41.7% wt % Zn and 28.4 wt % Ti (balance—oxygen). Total loading is 110 mg of zinc oxide per 100 mg of support ($TiO_2$).

Comparative Example 7

Prepared in the same way as Example 1, except the Total loading of zinc was 20 mg zinc oxide per 100 mg of support. The catalyst was calcined in air at 800° C. for 4 hrs.

Comparative Example 8

Prepared in the same way as Example 1, except the material was calcined in air at 1000° C. for 4 hrs.

Comparative Example 9

Prepared in the same way as Example 1, except the titania support was rutile (NORPRO, ST51122, BET surface area 3 m$^2$/g, pore volume 0.3 ml/g). Total loading of zinc was 4 mg zinc oxide per 100 mg of support. The catalyst was calcined in air at 400° C. for 4 hrs.

Comparative Example 10

A bulk catalyst was prepared by a thermal decomposition of a mixture of precursors. Two stock solutions were prepared: zinc nitrate in water at a concentration of 0.5 mol/l and titanium(IV) bis(ammonium lactato)dihydroxide at a concentration of 2.077 mol/l. The target atomic Ti/Zn ratio was 8/1.

The two stock solutions were mixed in the proportion required to achieve Ti/Zn atomic ratio of 8. For this 1 ml of zinc nitrate stock solution was mixed with 33.232 ml of titanium(IV) bis(ammonium lactato)dihydroxide solution. Deionized water was added to the solution in the volume equal to 1.6 times of the mixed stock solution. The as-prepared solution was heated to 90° C. with constant shaking (500 rpm) to evaporate the water. A solid material was obtained. The as-prepared material was dried and calcined using the following steps: (1) heated from RT to 120° C. at 2° C./min; (2) dwell for 2 hrs; (3) heated from 120° C. to 400° C. at 2° C./min; (4) dwell for 4 hrs; and (5) cooled down to RT in 2 hrs. After calcination the catalyst was pelletized, crushed and sieved to 60-80 mesh size.

Comparative Example 11

Prepared in the same way as Comparative Example 10, except the Ti/Zn atomic ratio was 1/2.

Comparative Example 12

A bulk catalyst was prepared by a co-precipitation method. Zinc nitrate was a source of zinc and titanium isopropoxide was a source of Ti. The Ti/Zn atomic ratio was 1/1.

Titanium isopropoxide solution in iso-propanol was prepared at a concentration of 0.984 mol/l (#1). Zinc nitrate solution in deionized water was prepared at a concentration of 2.0125 mol/l (#2). Ammonium Carbonate solution in deionized water was prepared at a concentration of 1.5 mol/l (#3).

To a 200 ml glass beaker, 60 ml of solution (#1) was added. At room temperature and with vigorous stirring, solutions (#2, 40 ml) and (#3, 30 ml) were added to the beaker. The white slurry was formed immediately and stirred for 1 hr at room temperature. The material was separated by centrifugation, dried and calcined on air according to the following steps: (1) heated from RT to 120° C. at 2° C./min; (2) dwell for 2 hrs; (3) heated from 120° C. to 400° C. at 2° C./min; (4) dwell for 4 hrs; and (5) cooled down to RT in 2 hrs. After calcination the catalyst was pelletized, crushed and sieved to 60-80 mesh size.

Comparative Example 13

A catalyst was prepared by a ball milling method. Powder of zinc oxide (693 mg, 852 mmol, surface area 23 m$^2$/g) and titanium dioxide (297 mg, 3.71 mmol, NORPRO, anatase, ST31119, surface area 40 m$^2$/g) were mixed together to form a physical mixture with a Ti/Zn atomic ratio of 1/2. The as-prepared material was subjected for ball milling (frequency 90/s) for 16 hrs. The as-prepared material had a structure of spinel $Zn_2TiO_4$ (confirmed by XRD). The catalyst was pelletized, crushed, and sieved to 60-80 mesh size.

Comparative Example 14

Zinc titanate with formula $ZnTiO_3$ (surface area 12 m$^2$/g) was purchased from a commercial vendor (Sigma-Aldrich) and used as received. The catalyst was pelletized, crushed and sieved to 60-80 mesh size.

Comparative Example 15

A catalyst was prepared by a co-precipitation method. Two separate stock solutions were prepared: zinc nitrate in deionized water with a concentration of 1 mol/l and titanium(IV) bis(ammonium lactato)dihydroxide at a concentration of 2.077 mol/l. A solution of Ammonium carbonate in water was prepared at a concentration of 1.6529 M and used as a precipitating agent. The atomic ratio of Ti/Zn in the catalyst was 1/2.

Precipitation was conducted at 55° C. with continuous stirring (500 rpm). Deionized water (10 ml) was added to a vial. Subsequently, zinc nitrate solution (11.54 ml) and titanium(IV) bis(ammonium lactato)dihydroxide solution (1.39 ml) were added dropwise from two different doping funnels while simultaneously adding the ammonium carbonate solution dropwise to keep pH of the mixture at 7.5±0.1. Total addition time of solution was 15 min. Subsequently, the slurry was aged at 55° C. for 2 hrs, filtered, and washed with deionized water. The as-prepared material was dried and calcined on air according to the following steps: (1) heated from RT to 120° C. at 2° C./min; (2) dwell for 2 hrs; (3) heated from 120° C. to 400° C. at 2° C./min; (4) dwell for 4 hrs; and (5) cooled down to RT in 2 hrs. After calcination the catalyst was pelletized, crushed, and sieved to 60-80 mesh size.

Comparative Example 16

Prepared in the same way as Example 1, except the support was tin (IV) oxide (pore volume determined to be 0.15 ml/g). Total loading of zinc was 2 mg (zinc oxide) per 100 mg of support.

Comparative Example 17

Prepared in the same way as Example 1, except the support was magnesium oxide (BET surface area 12 m$^2$/g, pore volume determined to be 0.5 ml/g). Total loading of zinc was 4 mg (zinc oxide) per 100 mg of support.

Comparative Example 18

Prepared in the same way as Example 1, except the support was aluminum oxide (NORPRO, gamma, SA6176, BET surface area 250 m$^2$/g, pore volume determined to be 1.06 ml/g). Total loading of zinc was 4 mg (zinc oxide) per 100 mg of support.

Comparative Example 19

Prepared in the same way as Example 1, except the support was titanium oxide (NORPRO, rutile, ST51122, BET surface area 3 m$^2$/g, pore volume determined to be 0.38 ml/g). Total loading of zinc was 1 mg (zinc oxide) per 100 mg of support.

Comparative Example 20

Prepared in the same way as Example 1, except that zinc was replaced with molybdenum. Ammonium molybdate (VI) tetrahydrate was used as Mo source. A stock solution with a concentration of 0.0714 mol/l was prepared. Total loading of molybdenum was 3 mg (molybdenum (VI) oxide) per 100 mg of support.

Comparative Example 21

Prepared in the same way as Example 1, except that zinc was replaced with tungsten. Ammonium metatungstate hydrate was used as W source. A stock solution with a concentration of 0.0417 mol/l was prepared. Total loading of tungsten was 3 mg tungsten (VI) oxide per 100 mg of support.

Comparative Example 22

Prepared in the same way as Example 1, except that the titania support was replaced with a sulfated titania support (pore volume 0.57 ml/g).

The sulfated titania support was formed by impregnating 1 g of titanium oxide support (NORPRO, Anatase, ST61120, BET surface area 130 m²/g, pore volume determined to be 0.57 ml/g, 60-80 mesh size) with 0.6 ml of 0.91 M $H_2SO_4$ in water to achieve loading of 5 mg ($SO_4$) per 100 mg of support. The impregnated support was dried and calcined on air according to the following steps: (1) heated from RT to 120° C. at 2° C./min; (2) dwell for 2 hrs; (3) heated from 120° C. to 400° C. at 2° C./min; (4) dwell for 4 hrs; and (5) cooled down to RT in 2 hrs.

Comparative Example 23

Prepared in the same way as Comparative Example 22, except that zinc was replaced with copper. A copper (II) nitrate solution was used as a source of Cu (stock solution with a concentration of 2 mol/l was used). Loading of Cu was 4 mg copper (II) oxide per 100 mg of support.

Comparative Example 24

Prepared in the same way as Example 1, except that the zinc loading was 0.5 mg zinc oxide per 100 mg of support.

Comparative Example 25

Prepared in the same way as Example 6, except that the support was silica (NORPRO, SS61138, BET surface area 250 m²/g, pore volume determine to be 1.2 ml/g); and chromium was replaced with titanium (IV) bis(ammonium lactato)dihydroxide with a concentration of 2.077 mol/l was. Total loading of oxides was 16 mg of ($TiO_2$+ZnO) per 100 mg of support. The atomic Ti/Zn ratio was 8/1.

Comparative Example 26

Prepared in the same way as Comparative Example 25, except that the atomic ratio of Ti/Zn was 1/2.

Comparative Example 27

Prepared in the same way as Example 9, except that the ammonium sulfate was replaced with ammonium chloride. Total loading of zinc was 4 mg zinc oxide per 100 mg of support. The atomic ratio of Cl/Zn was 15/100.

Comparative Example 28

A commercially available bulk CuZnAl mixed metal oxide catalyst (HiFUEL™ R120) that has a Cu content of 51 wt %, a Zn content of 20 wt %, and an Al content of 5 wt % was used as the methanol synthesis catalyst.

Comparative Example 29

A Cu/CrZn catalyst was prepared by depositing a solution of $Cu(NO_3)_2 \cdot 3H_2O$ on bulk CrZn mixed metal oxide catalyst following the incipient wetness impregnation method. The total Cu loading was 10 wt %.

Bulk CrZn mixed metal oxide catalyst was prepared by following the co-precipitation method. Targeting a Cr to Zn molar ratio of 0.4:1, appropriate quantities of $Cr(NO_3)_3 \cdot 9H_2O$ (16.1 g) and $Zn(NO_3)_2 \cdot 6H_2O$ (29.9 g) were added to 20 ml of distilled water ($H_2O$) and stirred until salts fully dissolved. In addition, a 0.5 M solution of $(NH_4)_2CO_3$ was prepared as a precipitating agent. The cation ($Cr^{3+}/Zn^{2+}$) and anion (($CO_3)^{2-}$) solutions were simultaneously added dropwise to a stirred beaker of distilled $H_2O$ maintained at $7.0 \leq pH \leq 7.5$ and T=65±5° C. Co-precipitated materials were filtered, washed with distilled water, dried in static air at 120° C., and subsequently calcined at 600° C. for 2 hrs.

A solution was made of 1.0558 g $Cu(NO_3)_2 \cdot 3H_2O$ in 2.25 ml of distilled water ($H_2O$). This solution (2.25 ml) was used to impregnate copper onto 2.5 g of the bulk CrZn catalyst. After impregnation, the sample was dried overnight at 120° C. followed by calcination in static oven at 400° C. for 4 hours.

Comparative Example 30

Bulk CrZn mixed metal oxide catalyst with a Cr to Zn molar ratio of 0.4:1 was prepared by following the co-precipitation method as described in Comparative Example 29.

Comparative Example 31

Zinc oxide (1 g, 60-80 mesh size, BET surface area 23 m²/g, pore volume 0.24 cm³/g), was impregnated with 0.24 ml of DI water using a standard incipient wetness impregnation method. The as-prepared material was dried and calcined using the following steps: (1) heated from RT to 120° C. at 2° C./min; (2) dwell for 2 hrs; (3) heated from 120° C. to 400° C. at 2° C./min; (4) dwell for 4 hrs; and (5) cooled down to RT in 2 hrs. After calcination the catalyst was re-sieved to 60-80 mesh size to remove fine particles.

Comparative Example 32

Zinc oxide (1.74 g, 60-80 mesh size, BET surface area 23 m²/g, pore volume 0.24 cm3/g), was impregnated with 0.42 ml of Titanium(IV) iso-propoxide (IPA) using a standard incipient wetness impregnation method. The as prepared material was dried and calcined using the following steps: (1) heated from RT to 120° C. at 2° C./min; (2) dwell for 2 hrs; (3) heated from 120° C. to 400° C. at 2° C./min; (4) dwell for 4 hrs; and (5) cooled down to RT in 2 hrs. After calcination, the catalyst was re-sieved to 60-80 mesh size to remove fine particles. Elemental analysis (XRF) showed that the material contains 5.0 wt % Ti and 73.5 wt % Zn (balance—oxygen). Total loading was 9 mg per 100 mg support (ZnO).

Comparative Example 33

A mixture of 55.7 mg (50 µl) of zinc oxide (60-80 mesh size, BET surface area 23 m²/g) and 53.3 mg (100 µl) of $TiO_2$ (60-80 mesh size, NORPRO ST61120, Anatase, BET surface area 130 m²/g) yielding 150 µl of a physical mixture of ZnO and $TiO_2$.

The compositions of the methanol synthesis components provided in Examples 1-24 and Comparative Examples 1-33 are provided in Table 1 and Table 2, respectively.

TABLE 2

Composition of Comparative Examples 1-33

| Comparative Example | M1 | M2 | M3 | M1, at fraction* | M2, at fraction | Total oxide loading per support, mg/100 mg of support | Type | Support | Titania Phase |
|---|---|---|---|---|---|---|---|---|---|
| 1 | Cu | Zn | Al | 61.5 | 23.5 | — | bulk | — | — |
| 2 | Zn | Cr | — | 0.7143 | 0.2857 | 20 | supported | silica | — |
| 3 | Zn | Cr | — | 0.3334 | 0.6666 | 20 | supported | silica | — |
| 4 | Zn | Cr | — | 0.7143 | 0.2857 | 4 | supported | ceria | — |
| 5 | Zn | Cr | — | 0.3334 | 0.6666 | 4 | supported | ceria | — |
| 6 | Zn | — | — | 1 | — | 110 | supported | titania | Anatase |
| 7 | Zn | — | — | 1 | — | 10 | supported | titania | Anatase |
| 8 | Zn | — | — | 1 | — | 10 | supported | titania | Anatase |
| 9 | Zn | — | — | 1 | — | 4 | supported | titania | Rutile |
| 10 | Zn | Ti | — | 0.111 | 0.889 | — | bulk | — | — |
| 11 | Zn | Ti | — | 0.667 | 0.333 | — | bulk | — | — |
| 12 | Zn | Ti | — | 0.5 | 0.5 | — | bulk | — | — |
| 13 | Zn | Ti | — | 0.667 | 0.333 | — | bulk | — | — |
| 14 | Zn | Ti | — | 0.5 | 0.5 | — | bulk | — | — |
| 15 | Zn | Ti | — | 0.667 | 0.333 | — | bulk | — | — |
| 16 | Zn | — | — | 1 | — | 2 | supported | tin oxide | — |
| 17 | Zn | — | — | 1 | — | 4 | supported | magnesia | — |
| 18 | Zn | — | — | 1 | — | 4 | supported | alumina | gamma |
| 19 | Zn | — | — | 1 | — | 1 | supported | titania | Rutile |
| 20 | Mo | — | — | 1 | — | 3 | supported | titania | Anatase |
| 21 | W | — | — | 1 | — | 3 | supported | titania | Anatase |
| 22 | Zn | — | — | 1 | — | 4 | supported | sulfated titania | Anatase |
| 23 | Cu | — | — | 1 | — | 4 | supported | sulfated titania | Anatase |
| 24 | Zn | — | — | 1 | — | 0.5 | supported | titania | Anatase |
| 25 | Zn | Ti | — | 0.111 | 0.889 | 16 | supported | silica | — |
| 26 | Zn | Ti | — | 0.667 | 0.333 | 16 | supported | silica | — |
| 27 | Zn | Cl | — | 1 | — | 4 | supported | titania | Anatase |
| 28 | Same as Comparative Example 1 | | | | | | | | |
| 29 | Cu | — | — | | | | supported/bulk | Cr4ZnlO | — |
| 30 | Zn | Cr | — | 0.7143 | 0.2857 | | bulk | — | — |
| 31 | Zn | — | — | | | | bulk | — | — |
| 32 | Ti | — | — | | | | supported | zinc oxide | — |
| 33 | Zn | Ti | — | 0.505 | 0.495 | | bulk | — | — |

| Comparative Example | Support surface area, m²/g | M1 mmol/g support | M2 mmol/g support | Zn/Ti at/at | Calcination T, °C. |
|---|---|---|---|---|---|
| 1 | — | — | — | — | — |
| 2 | 295 | 1.79 | 0.716 | — | 500 |
| 3 | 295 | 0.86 | 1.72 | — | 500 |
| 4 | 68 | 0.358 | 0.143 | — | 400 |
| 5 | 68 | 0.172 | 0.344 | — | 400 |
| 6 | 130 | 13.44 | — | 1.07 | 400 |
| 7 | 40 | 0.489 | — | 0.098 | 800 |
| 8 | 40 | 0.489 | — | 0.098 | 1000 |
| 9 | 3 | 0.489 | — | 0.0391 | 400 |
| 10 | — | — | — | 0.125 | 400 |
| 11 | — | — | — | 2 | 400 |
| 12 | — | — | — | 1 | 400 |
| 13 | — | — | — | 2 | — |
| 14 | — | — | — | 1 | — |
| 15 | — | — | — | 2 | 400 |
| 16 | n.d. | 0.245 | — | — | 400 |
| 17 | 12 | 0.489 | — | — | 400 |
| 18 | 250 | 0.489 | — | — | 400 |
| 19 | 3 | 0.122 | — | 0.0098 | 400 |
| 20 | 130 | 0.208 | — | — | 400 |
| 21 | 130 | 0.129 | — | — | 400 |
| 22 | 130 | 0.489 | — | 0.0391 | 400 |
| 23 | 130 | 0.502 | — | — | 400 |
| 24 | 130 | 0.06 | — | 0.0049 | 400 |
| 25 | 250 | 0.22 | 1.78 | 0.125 | 400 |

TABLE 2-continued

Composition of Comparative Examples 1-33

| | | | | | |
|---|---|---|---|---|---|
| 26 | 250 | 1.33 | 0.653 | 2 | 400 |
| 27 | 130 | 0.489 | 0.073 | 0.0391 | 400 |
| 28 | | | | | |
| 29 | — | 1.74 | | — | 400 |
| 30 | | | | | 400 |
| 31 | | — | — | — | 400 |
| 32 | 23 | 1.12 | — | 10.9 | 400 |
| 33 | — | — | — | 1.02 | — |

*For metal fraction calculations metal loadings were considered, not oxides

Preparation of the Methanol Synthesis Component with SAPO-34

Methanol synthesis components prepared as described in Examples 1-14 and 18-25 and Comparative Examples 1-27 and 31-33 were mixed with SAPO-34 (calcined at 600° C. for 4 hrs, 60-80 mesh size) volumetrically in equal proportion 50/50 vol/vol. For this purpose, 150 µl of a material was mixed with 150 µl of SAPO-34. The mixture was well shaken to ensure equal distribution of particles in the physical mixture.

Materials prepared as described in Examples 15-17 and Comparative Examples 28-30 were mixed with SAPO-34 (calcined at 600° C. for 4 hrs, 40-80 mesh size). For the catalytic performance tests, 1 gram of methanol catalyst component was physically mixed with 0.5 grams of SAPO-34 catalyst by shaking them together in a bottle. Each of the catalysts had a particle size before mixing within a range of from 40 mesh (0.422 millimeter) to 80 mesh (0.178 millimeter).

Catalytic Test of Examples 1-14 and 18-25 or Comparative Examples 1-27 and 31-33

Catalyst test were performed in a tubular stainless steel fixed-bed microreactor. The bottom of the stainless steel reactor was equipped with a metal frit. Total hybrid bed loading was 300 µl. Products were analyzed by gas chromatography. Online analysis of components ($N_2$, $H_2$, He, CO, $CO_2$, $C_1$-$C_5$ alkanes, $C_2$-$C_5$ olefins) was performed periodically to monitor the reaction progress. Mass balance in all experiments was 95-100% based on carbon. No activation step was required prior to catalyst testing. The following procedure was used for measuring catalytic activity of hybrid physical mixture in conversion of syngas to light olefins:

1) $N_2$ flow, 6 ml/min, ambient pressure, heated from 25° C. to 390° C. at 5° C./min;
2) $N_2$ flow, 6 ml/min, pressurized from ambient pressure to 20 bar, at 390° C.;
3) $N_2$ changed to syngas 60 vol % $H_2$, 30 vol % CO, 10 vol % He, 6 ml/min, 20 bar, 390° C.;
4) Syngas, 6 ml/min, 20 bar, 390° C., flushing for 1 hour;
5) Reacting syngas, 6 ml/min, 20 bar, 390° C., GC analysis start up—defined as time on stream "zero";
6) Duration of the run was 70-100 hrs time on stream; and
7) Syngas to $N_2$, 6 ml/min, cooling down to room temperature, end of the run.

Catalytic Test of Example 15-17 or Comparative Example 28-30

Catalytic tests were performed in a tubular fixed bed reactor. The physically mixed catalysts were activated at conditions indicated in Table 3. The system was then purged with pure nitrogen. Afterwards, the system was heated up and pressurized to the reaction temperature and pressure under a continuous nitrogen flow. The flow of nitrogen was switched off and certain amounts of CO, $H_2$ and He were passed over the catalyst to reach the feed ratio and weight hourly space velocity (WHSV) as indicated in Table 3.

TABLE 3

Process conditions applied during catalytic performance testing

| Examples | Catalyst | Activation conditions | Reaction temp (° C.) | Reaction pressure (bar) | Feed $H_2$/CO ratio | Cat. ratio | WHSV ($h^{-1}$) |
|---|---|---|---|---|---|---|---|
| Ex. 15 | CuCrZn/$TiO_2$ + SAPO-34 | 300° C., 10 bar, 6 hrs, pure $H_2$ (100 ml/min) | 400 | 50 | 3 | 2/1 | 1.4 |
| Ex. 16 | CuZn/$TiO_2$ + SAPO-34 | 300° C., 10 bar, 6 hours, pure $H_2$ (100 ml/min) | 400 | 50 | 3 | 2/1 | 1.4 |
| Ex. 17 | CrZn/$TiO_2$ + SAPO-34 | 300° C., 10 bar, 6 hours, pure $H_2$ (100 ml/min) | 400 | 50 | 3 | 2/1 | 1.4 |
| C. Ex. 28 | CuZnAl (bulk) + SAPO-34 | 270° C., 10 bar, 6 hours, pure $H_2$ (100 ml/min) | 400 | 50 | 3 | 2/1 | 1.4 |
| C. Ex. 29 | Cu/CrZn + SAPO-34 | 400° C., atmospheric pressure 2 hours $H_2$: 22.5 ml/min, $N_2$: 11.25 ml/min | 400 | 50 | 3 | 2/1 | 1.4 |
| C. Ex. 30 | CrZn0.4 (bulk) + SAPO-34 | 400° C., atmospheric pressure 2 hours $H_2$: 22.5 ml/min, $N_2$: 11.25 ml/min | 400 | 50 | 3 | 2/1 | 1.4 |

Catalytic data for the examples and comparative examples was provided in Table 4 and Table 5, respectively.

TABLE 4

Catalytic data for Examples 1-25

| Example | Conversion, % | $C_2$-$C_5$ olefin yield, % | $C_2$-$C_5$ paraffin yield, % | Methane Yield, % | Selectivity to $CO_2$, % | Integral olefin productivity, kg olefins/ l_cat |
|---|---|---|---|---|---|---|
| 1 | 24.7 | 8.9 | 3.4 | 1.2 | 45.4 | 6.9 |
| 2 | 23.9 | 7.4 | 3.5 | 1.7 | 47.7 | 4.6 |
| 3 | 20.9 | 6.8 | 3.3 | 1.3 | 45.6 | 4.3 |
| 4 | 22.1 | 7.2 | 3.6 | 1.5 | 44.4 | 13.6 |
| 5 | 16.7 | 3.6 | 4.5 | 1.2 | 44.8 | 2.7 |
| 6 | 18.5 | 6.0 | 3.2 | 1.3 | 43.6 | 18.5 |
| 7 | 22.9 | 8.9 | 2.2 | 1.1 | 46.8 | 10.0 |
| 8 | 23.7 | 8.8 | 2.9 | 1.1 | 46.3 | 4.6 |
| 9 | 24.6 | 8.8 | 3.4 | 1.2 | 45.8 | 6.7 |
| 10 | 25.8 | 8.8 | 3.5 | 1.4 | 46.3 | 10.7 |
| 11 | 22.6 | 8.3 | 3.0 | 1.0 | 45.4 | 3.4 |
| 12 | 23.1 | 8.1 | 2.9 | 1.3 | 46.7 | 3.6 |
| 13 | 21.6 | 7.4 | 2.8 | 1.1 | 46.7 | 23.3 |
| 14 | 23.0 | 8.6 | 2.9 | 1.1 | 44.9 | 7.3 |
| 15 | 44.4 | 8.0 | 15.0 | 5.2 | 36.2 | 20.1 |
| 16 | 43.2 | 4.5 | 21.8 | 2.5 | 33.2 | 6.9 |
| 17 | 33.2 | 4.5 | 10.5 | 3.1 | 43.2 | 32.0 |
| 18 | 40.9 | 15.0 | 5.0 | 1.5 | 47.4 | 14.0 |
| 19 | 33.5 | 10.5 | 6.2 | 1.0 | 47.1 | 8.2 |
| 20 | 32.3 | 11.5 | 4.2 | 1.6 | 47.4 | 5.7 |
| 21 | 37.3 | 8.4 | 9.2 | 2.9 | 44.9 | 5.9 |
| 22 | 26.9 | 9.2 | 3.2 | 1.1 | 49.6 | 28.5 |
| 23 | 18.2 | 4.0 | 3.4 | 1.6 | 50 | 5.5 |
| 24 | 24.3 | 8.2 | 4.22 | 1.0 | 45 | 7.1 |
| 25 | 19.3 | 4.5 | 3.5 | 1.8 | 49.0 | 3.0 |

TABLE 5

Catalytic data for Comparative Examples 1-33

| Comparative Example | Conversion, % | $C_2$-$C_5$ olefin yield, % | $C_2$-$C_5$ paraffin yield, % | Methane Yield, % | Selectivity to $CO_2$, % | Integral olefin productivity, kg olefins/ l_cat |
|---|---|---|---|---|---|---|
| 1 | 58.3 | 0.0 | 27.9 | 2.9 | 47.0 | 0.0 |
| 2 | 6.7 | 0.0 | 1.8 | 2.1 | 42.0 | 0.0 |
| 3 | 5.8 | 0.2 | 1.4 | 2.4 | 36.5 | 0.2 |
| 4 | 9.2 | 0.4 | 3.9 | 0.7 | 46.6 | 0.1 |
| 5 | 9.1 | 1.5 | 2.5 | 0.7 | 48.2 | 0.4 |
| 6 | 18.2 | 4.6 | 4.0 | 1.3 | 44.8 | 2.0 |
| 7 | 3.2 | 0.2 | 0.6 | 1.0 | 40.7 | 0.3 |
| 8 | 1.9 | 0.3 | 0.3 | 0.6 | 36.7 | 0.7 |
| 9 | 7.0 | 0.3 | 1.7 | 2.1 | 40.9 | 0.1 |
| 10 | 8.7 | 1.6 | 2.5 | 1.4 | 37.2 | 0.4 |
| 11 | 14.1 | 0.2 | 5.0 | 2.6 | 43.6 | 0.1 |
| 12 | 24.2 | 0.3 | 11.2 | 2.2 | 43.4 | 0.2 |
| 13 | 12.4 | 0.7 | 5.4 | 1.0 | 42.8 | 0.2 |
| 14 | 14.3 | 0.4 | 7.1 | 1.0 | 41.2 | 1.2 |
| 15 | 14.4 | 0.5 | 7.0 | 0.9 | 42.3 | 0.3 |
| 16 | 4.9 | 0.2 | 1.2 | 1.2 | 46.2 | 0.0 |
| 17 | 8.0 | 0.3 | 1.7 | 2.2 | 46.6 | 0.1 |
| 18 | 10.9 | 1.4 | 2.8 | 1.3 | 51.3 | 2.4 |
| 19 | 3.4 | 0.1 | 1.0 | 0.7 | 44.7 | 0.1 |
| 20 | 22.5 | 0.1 | 5.9 | 5.6 | 48.6 | 0.1 |
| 21 | 2.2 | 0.2 | 0.4 | 0.6 | 45.2 | 0.4 |
| 22 | 14.8 | 1.8 | 4.1 | 1.7 | 49.2 | 2.5 |
| 23 | 1.4 | 0.1 | 0.2 | 0.5 | 49.2 | 0.1 |
| 24 | 3.5 | 0.4 | 0.6 | 0.7 | 49.2 | 1.1 |
| 25 | 7.1 | 1.3 | 1.8 | 0.7 | 45.8 | 1.4 |
| 26 | 5.0 | 0.3 | 1.7 | 0.8 | 42.9 | 0.1 |
| 27 | 15.9 | 5.3 | 2.4 | 0.8 | 46.7 | 1.7 |
| 28 | 81.0 | 0.0 | 49.5 | 2.5 | 35.7 | 0.0 |

TABLE 5-continued

Catalytic data for Comparative Examples 1-33

| Comparative Example | Conversion, % | $C_2$-$C_5$ olefin yield, % | $C_2$-$C_5$ paraffin yield, % | Methane Yield, % | Selectivity to $CO_2$, % | Integral olefin productivity, kg olefins/ l_cat |
|---|---|---|---|---|---|---|
| 29 | 69.0 | 0.0 | 37.1 | 4.9 | 39.1 | 0.0 |
| 30 | 64.0 | 1.0 | 33.5 | 5.0 | 38.3 | 1.3 |
| 31 | 20.8 | 4.9 | 4.4 | 1.3 | 48.6 | 1.7 |
| 32 | 16.6 | 1.7 | 5.5 | 1.5 | 47.3 | 0.7 |
| 33 | 11.4 | 2.2 | 2.2 | 1.3 | 50.0 | 2.9 |

Examples 1-3 and Example 23 show that a hybrid catalyst containing Zn supported on high surface area titania support (130 m²/g, Zn/Ti at/at ratio 0.01-0.39) as methanol synthesis component has a high activity in conversion of syngas to olefins. Thus, the methanol synthesis components containing zinc and titanium (Zn—Ti) were active in activation of synthesis gas and in the production of oxygenates (methanol, dimethyl ether) which were simultaneously converted over SAPO-34 to short chain olefins. Zn—Ti catalysts also have low hydrogenation activity towards olefins. This feature renders Zn—Ti materials excellent components for hybrid catalyst.

Example 4 shows that zinc can be deposited on anatase titania with moderate surface area (40 m²/g).

Example 5 shows that zinc can be deposited on a rutile phase of titania (100% rutile, surface area around 100 m²/g). However, surface area matters; compare with low surface area rutile titania supports in Comparative Examples 9 and 19, which did not have good activity.

The yield of olefins in the case of zinc supported on pure anatase titania was higher than for anatase-rutile supported methanol synthesis components; compare Example 1 and Example 5.

Example 6 and 7 show that that the addition of other metals (Cr, Mn) to Zn/TiO₂ methanol synthesis components can improve olefin productivity of the hybrid catalyst; compare Example 1 (Zn/TiO₂), Example 6 (Zn—Cr/TiO₂), and Example 7 (Zn—Mn/TiO₂).

The addition of non-metallic elements to Zn/TiO₂ methanol synthesis components can improve performance of the hybrid catalyst. For instance, the sulfur (in the form of $SO_4^{2-}$ (S/Zn at/at 15/100) in Example 8 or sulfide $S^{2-}$ (S/Zn at/at 10/100) in Example 9; the phosphorous $PO_4^{3-}$ (P/Zn at/at 15/100) in Example 11; the boron (B/Zn at/at 15/100) in Example 12; the halides (chloride Cl/Zn at/at 5/100) in Example 13; and the alkaline elements Potassium (K/Zn at/at 10/100) in Example 14.

Example 10 shows that the deposition of zinc on anatase titania containing 3 wt % Ca and 2 wt % S resulted in an active methanol synthesis component and the hybrid catalyst has high activity (conversion 25.8%) and high olefin yield (8.8%).

Examples 15 and 16 demonstrate that Cu can also be used as an active element when deposited on TiO₂ support. These methanol synthesis components remain active towards olefin production even at a higher H₂/CO feed ratio of 3 and total pressure of 50 bar.

Example 17 demonstrates that TiO₂ supported methanol synthesis component in combination with SAPO-34 was active in production of olefins even at a higher H₂/CO ratio of 3 and pressure of 50 bar.

Examples 18-22 show that zinc can also be supported on zirconia (ZrO₂) to form an active methanol synthesis component and a combination of such methanol synthesis component with SAPO-34 results in highly active hybrid catalyst enabling the production of olefins. Monoclinic, tetragonal zirconia can be used as shown by Examples 18 and 19, respectively. Example 20 shows that a mixed phase of zirconia-titania can also be used as a support for zinc. Examples 21 and 22 show that zirconia with dopants such as La or sulfate can also be used as a support.

Example 24 shows that anatase TiO₂ with surface area>130 m²/g can also be used as supports for Zn.

Comparative Example 1 shows a hybrid catalyst that was prepared using an industrial Cu-based methanol synthesis catalyst HiFuel™ and SAPO-34. While a combination of Cu-based methanol synthesis catalyst with SAPO-34 results in the production of hydrocarbons with high activity, no olefins were observed in the reaction mixture.

Comparative Examples 2-5, 16, 17, 18, show that deposition of Zn (with or without Cr) onto other carriers such as silica, ceria, tin oxide, magnesia, or alumina results in methanol synthesis components that have lower activity and/or olefin production than titania or zirconia supported systems (see Examples 1-22). Comparative Examples 25 and 26 show that deposition of Zn—Ti by co-impregnation on silica does not results in a good catalytic performance.

Comparative Example 6 shows that too high Zn loading onto titania results in lower performance of the methanol synthesis component with respect to olefin productivity; compare Example 1 and Comparative Example 6.

Comparative Example 24 shows that Zn/Ti at/at ratio may, in embodiments, be >0.0049, and Comparative Example 6 shows that Zn/Ti at/at ratio may, in embodiments, be <1.07 to form an active material with high catalytic activity and olefin productivity.

Comparative Examples 7 and 8 show that calcination temperature has an effect on methanol synthesis component performance. Calcination of Zn/TiO₂ at 800° C. or 1000° C. results in a low activity of methanol synthesis component in the hybrid mixture compared to calcination at 400° C.; compare Example 1 to Comparative Example 7 and Comparative Example 8.

The phase of titania in the Zn—Ti methanol synthesis component plays a role in the performance of the hybrid catalysts. Examples 1-4 demonstrate that anatase titania was advantageous compared to mix phase anatase-rutile (see Example 5). Rutile enriched titania as well as pure rutile were less active supports for zinc (see Comparative Examples 9 and 19).

Comparative Examples 10-15 show that bulk Zn—Ti methanol synthesis component in combination with SAPO- 34 have lower performance compared to supported Zn—Ti systems (see Examples 1-17).

Comparative Examples 20 and 21 show that deposition of such elements as Mo or W onto anatase titania does not result in a methanol synthesis component that has a high activity and olefin productivity in the hybrid mixture with SAPO-34.

Comparative Examples 22-23 show that deposition of 4 wt % $SO_4$ onto titania as using sulfated titania as carrier for zinc or copper result in a methanol synthesis component with low performance.

Comparative Example 27 shows that Cl has detrimental effect on catalyst performance when Zn/Cl ratio was <20 (see Comparative Example 27 where Zn/Cl=6.7, while in Example 13 Zn/Cl=20).

Comparative Example 31 shows that ZnO in combination of SAPO-34 does not have the same performance as $Zn/TiO_2$ or $Zn/ZrO_2$ (see Example 1 and Example 18).

Comparative Example 32 shows that reversed impregnation of ZnO with Ti results in a methanol synthesis component that has low activity (16.6% conversion) and low olefin productivity (0.7 kg olefin/l cat).

Comparative Example 33 shows that a physical mixture of ZnO and $TiO_2$ does not have same performance as Zn impregnated onto a titania support (see Example 1).

It will be apparent to those skilled in the art that various modifications and variations can be made to the embodiments described herein without departing from the spirit and scope of the claimed subject matter. Thus it was intended that the specification cover the modifications and variations of the various embodiments described herein provided such modification and variations come within the scope of the appended claims and their equivalents.

The invention claimed is:

1. A process for preparing $C_2$ to $C_5$ olefins, comprising:
    introducing a feed stream comprising hydrogen and at least one carbon-containing component selected from the group consisting of CO, $CO_2$, and mixtures thereof into a reaction zone;
    contacting the feed stream with a hybrid catalyst in the reaction zone to synthesize C2 to C5 olefins, wherein the hybrid catalyst comprises a methanol synthesis component and a solid microporous acid component that is selected from molecular sieves having 8-MR access and having a framework type selected from the group consisting of the following framework types CHA, AEI, AFX, ERI, LTA, UFI, RTH, and combinations thereof, the framework types corresponding to the naming convention of the International Zeolite Association, wherein the methanol synthesis component comprises a metal oxide support and a metal catalyst, wherein the metal oxide support comprises titania, zirconia, hafnia or mixtures thereof, and the metal catalyst comprises zinc; and
    forming a product stream that exits the reaction zone, wherein the product stream comprises $C_2$ to $C_5$ olefins.

2. The process according to claim 1, wherein a surface area of the metal oxide support is greater than or equal to 20 $m^2/g$.

3. The process according to claim 1, wherein the metal oxide support comprises titania or a mixture of titania and zirconia.

4. The process according to claim 1, wherein the solid microporous acid component is SAPO-34.

5. The process according to claim 1, wherein the metal catalyst further comprises copper, chromium, manganese, and mixtures thereof.

6. The process according to claim 1, wherein a loading of the metal catalyst, measured per 100 mg of metal oxide support, is from greater than or equal to 0.8 mg of metal catalyst/100 mg of metal oxide support to less than or equal to 50.0 mg of metal catalyst/100 mg of metal oxide support.

7. The process according to claim 1, wherein the metal oxide support comprises titania and an atomic ratio (at/at) of zinc to titania (Zn/Ti) is from greater than or equal to 0.01 to less than or equal to 0.61, or the metal oxide support comprises zirconia and an atomic ratio (at/at) of zinc to zirconia (Zn/Zr) is from greater than or equal to 0.01 to less than or equal to 0.94.

8. The process according to claim 1, wherein the methanol synthesis component is calcined at a temperature less than 800° C.

9. The process according to claim 1, wherein a carbon monoxide conversion is greater than or equal to 15%.

10. The process according to claim 1, wherein a carbon yield of $C_2$ to $C_5$ olefins is greater than or equal to 3.6%.

11. The process according to claim 1, wherein an integral productivity of the hybrid catalyst is greater than or equal to 2.5 kg olefins/liter (l) of catalyst in 1000 h time.

* * * * *